United States Patent
Kamen

Patent Number: 5,983,136
Date of Patent: Nov. 9, 1999

[54] SYSTEM FOR DELIVERY OF DRUGS BY TRANSPORT

[75] Inventor: Dean L. Kamen, Bedford, N.H.

[73] Assignee: Deka Products Limited Partnership, Manchester, N.H.

[21] Appl. No.: 08/929,984

[22] Filed: Sep. 15, 1997

Related U.S. Application Data

[60] Provisional application No. 60/026,266, Sep. 17, 1996, and provisional application No. 60/039,036, Feb. 24, 1997.

[51] Int. Cl.$^6$ .............................. A61N 1/30; A61M 1/00
[52] U.S. Cl. ................................ 604/21; 604/35; 604/20
[58] Field of Search ........................... 604/20, 21, 891.1, 604/264, 272, 175, 239, 27, 28, 35, 19, 22, 51; 607/120, 126, 127, 128, 130, 131, 152; 428/901, 597, 315.9

[56] References Cited

U.S. PATENT DOCUMENTS

| | | | |
|---|---|---|---|
| 3,617,613 | 11/1971 | Benzinger et al. | 428/901 |
| 3,675,766 | 7/1972 | Rosenthal | 206/63.4 |
| 3,814,097 | 6/1974 | Ganderton et al. | 128/268 |
| 3,964,482 | 6/1976 | Gerstel et al. | 128/260 |
| 4,340,048 | 7/1982 | Eckenhoff | 128/213 R |
| 4,382,441 | 5/1983 | Svedman | 604/291 |
| 4,403,609 | 9/1983 | Cohen | 604/70 |
| 4,421,508 | 12/1983 | Cohen | 604/70 |
| 4,447,225 | 5/1984 | Taff et al. | 604/71 |
| 4,711,247 | 12/1987 | Fishman | 604/181 |
| 4,922,926 | 5/1990 | Hirschberg et al. | 604/93 |
| 5,080,648 | 1/1992 | D'Antonio | 604/72 |
| 5,153,986 | 10/1992 | Brauer et al. | 29/846 |
| 5,250,023 | 10/1993 | Lee et al. | 604/20 |
| 5,279,544 | 1/1994 | Gross et al. | 604/20 |
| 5,309,909 | 5/1994 | Gadsby et al. | 128/639 |
| 5,312,456 | 5/1994 | Reed et al. | 411/456 |
| 5,484,399 | 1/1996 | DiResta et al. | 604/21 |
| 5,702,359 | 12/1997 | Hofmann et al. | 604/20 |

FOREIGN PATENT DOCUMENTS

| | | | |
|---|---|---|---|
| 0 347 190 | 12/1989 | European Pat. Off. | |
| 2 221 394 | 7/1990 | United Kingdom | |
| WO 92/11879 | 7/1992 | WIPO | |
| WO 94/23777 | 10/1994 | WIPO | |
| WO 96/17648 | 6/1996 | WIPO | 604/20 |
| WO 97/07734 | 3/1997 | WIPO | 604/20 |
| WO 98/00193 | 1/1998 | WIPO | 604/20 |

Primary Examiner—Wynn Wood Coggins
Assistant Examiner—Sharon Finkel
Attorney, Agent, or Firm—Bromberg & Sunstein LLP

[57] ABSTRACT

A method and apparatus for introducing a fluid agent into body tissue by causing transport of the fluid agent into the dermis of the subject. The outer surface of the skin of the subject is drawn against a plurality of micropenetrators such that microfissures are cloven into the epidermis and fluid may be introduced for diffusion or suction within the dermis. Suction creates a pressure gradient within the dermis to cause fluid take-up by the dermal tissue. The micropenetrators are produced by punching an array of protrusions in the surface of a thin sheet creating sharp edges for penetrating the epidermis.

22 Claims, 6 Drawing Sheets

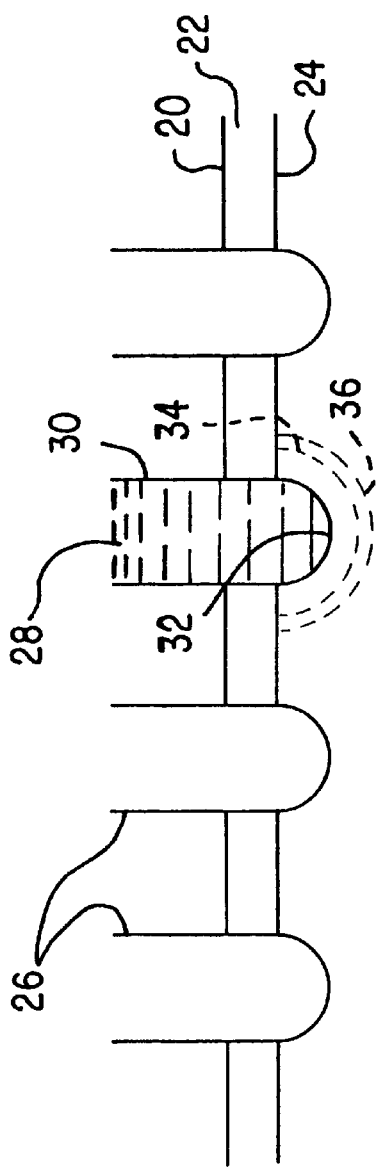
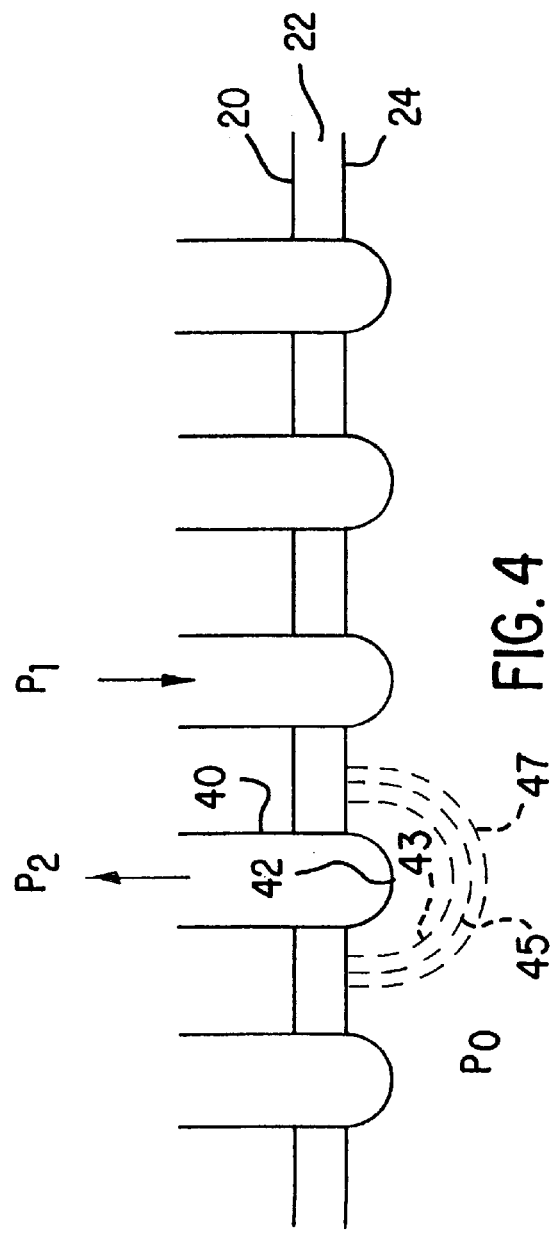
FIG. 3
FIG. 4

SYSTEM FOR DELIVERY OF DRUGS BY TRANSPORT

The present application claims priority from U.S. provisional application Ser. No. 60/026,266, filed Sep. 17, 1996, and from U.S. provisional application Ser. No. 60/039,036, filed Feb. 24, 1997, which are herein incorporated by reference.

TECHNICAL FIELD

The present invention pertains to a system for delivering therapeutic substances into the body, and, in particular, to a convenient method and device for providing transport of fluid with minimal invasion of the dermis.

BACKGROUND OF THE INVENTION

Delivery of therapeutic fluid agents through the skin requires penetration of the stratus corneum, the outer layer of the epidermis, and the layer of skin which normally provides a largely impervious barrier to the flow of microbes and most other materials into or out of the body. Penetration of the epidermal layer is conventionally accomplished by means of a hollow needle or cannula, beveled at the penetrating end so as to provide a sharp point for local shearing of the skin, both at the surface, and in the course of continued penetration, as the needle is driven down through the epidermal layers into the dermis. Some known methods apply suction around the injecting cannula to distend or engorge the underlying blood vessels, in order more efficiently to achieve intravenous infusion of material. Since the dermis contains live nerve cells, the penetration of the needle is often uncomfortable to a patient.

Among the methods known for introducing drugs or other therapeutic agents into the body, some employ a multiplicity of needles. The known methods employing multiple needles require devices which are difficult to fabricate and therefore costly.

Other methods are known in the art for introducing therapeutic agents into the dermis so that they can be taken up by the circulatory system and distributed within the body to clinical advantage. One such method is simple topical application, such as a patch, which relies upon slow diffusion of the agent through the epidermis. Another method employs a jet injector whereby one or more streams of fluid agent are driven forcibly through the epidermis without further mechanical separation of the outer tissue layer. These methods, reliant upon passage of fluid through the epidermis, provide highly indeterminate and variable rates of diffusion and thus of total quantity of agent introduced. In many applications, this indeterminacy is unacceptable, either because the therapeutic agent is dangerous or costly in quantities exceeding the desired concentration of the substance.

SUMMARY OF THE INVENTION

In accordance with one aspect of the invention, in one of its embodiments, there is provided a method for causing the transport, as defined below, of a substance across an outer boundary of a porous medium. The method includes the steps of creating a pressure gradient along at least one path, each path running from a first zone of the porous medium to a second zone of the porous medium proximate to the first zone, so that the pressure at the second zone is below ambient pressure at the outer surface of the porous medium and causing transport of the substance across the outer boundary of the porous medium through at least one microfissure, where the term "microfissure" is also defined below.

In alternate embodiments of the present invention, the may be drawn either into or out of the porous medium, the substance may be a liquid or a therapeutic agent, and the porous medium may be body tissue. The step of creating a pressure gradient may include puncturing at least one microfissure in the outer boundary of the porous medium with at least one micropenetrator. Additionally, the pressure gradient between zones of the porous medium may be created by applying suction to a portion of the outer surface of the porous medium, applying suction to a subset of the micropenetrators, and applying suction to a subset of the microfissures. In another embodiment of the present invention, at least one micropenetrator is drawn into contact with the outer surface of the porous medium by applying suction to a portion of the outer boundary of the porous medium substantially surrounding the contact between the micropenetrator and the outer boundary of the porous medium.

In accordance with a further aspect of the invention, there is provided an apparatus for causing the transport of a substance across the outer boundary of a porous medium. The apparatus has a platen with at least one orifice and at least one micropenetrator coupled to the platen for cleaving microfissures in the outer boundary of the porous medium. A vacuum arrangement is provided for creating a pressure gradient along at least one path, each path running from a first zone of the porous medium to a second zone of the porous medium proximate to the first zone, so that the pressure at the second zone is below ambient pressure at the outer boundary of the porous medium. A reservoir is also provided for supplying the substance to at least one micropenetrator so as to cause transport of the substance into the porous medium. In an alternative embodiment of the apparatus, there is provided a partial vacuum for drawing the outer surface of the porous medium against at least one micropenetrator, while, in further alternate embodiments, at least one sensor is provided, each sensor having an output, for monitoring the quantity of substance transported into the porous medium and a controller for regulating the rate of substance supplied by the reservoir based on the sensor outputs. Additionally, at least one sensor may be provided for monitoring a biological response to the transport of the substance across the outer boundary of the porous medium and a controller for regulating the rate at which the substance is supplied based on the sensor output.

In accordance with yet a further aspect of the invention, there is provided a method of manufacture for producing an apparatus for causing the transport of a substance across the outer boundary of a porous medium. The method includes the steps of punching an array of protrusions in the surface of a thin planar platen such as to create orifices in the platen, coupling a first plenum to a first subset of the orifices in the platen, and coupling a second plenum to a second set of the orifices in the platen. In an alternate embodiment of the invention, the protrusions punched in the surface of the thin planar platen are conical.

Another embodiment of the method-of-manufacture aspect of the invention provides an alternate method of manufacture for producing an apparatus for transporting a substance across the boundary of a porous medium. The method includes the steps of punching an array of peninsular tongues in the surface of a thin planar platen, depressing the peninsular tongues below the surface of the platen such as to create orifices in the platen, coupling a first plenum to a first subset of the orifices in the platen, and coupling a second plenum to a second set of the orifices in the platen.

The fluid transport system described herein advantageously provides the capability to introduce well-controlled and reproducible quantities of liquid agents through the epidermis without local trauma to the underlying dermis. An additional advantage of the present invention is to provide an inexpensive apparatus for introducing liquid agents through the epidermis. Other objects and advantages of the invention are in part apparent and in part pointed out hereinafter.

BRIEF DESCRIPTION OF THE DRAWINGS

The invention will be more readily understood by reference to the following description, taken with the accompanying drawings, in which:

FIG. 3 is a cross-sectional view showing a section of a row of the micropenetrators of FIG. 1 penetrating the skin and further showing contours of equal concentration of agent due solely to diffusion.

FIG. 4 is a cross-sectional view showing a section of a row of the micropenetrators of FIG. 1 penetrating the skin and further showing contours of equal pressure within the skin in the presence of suction.

DETAILED DESCRIPTION OF SPECIFIC EMBODIMENTS

Figure 1:
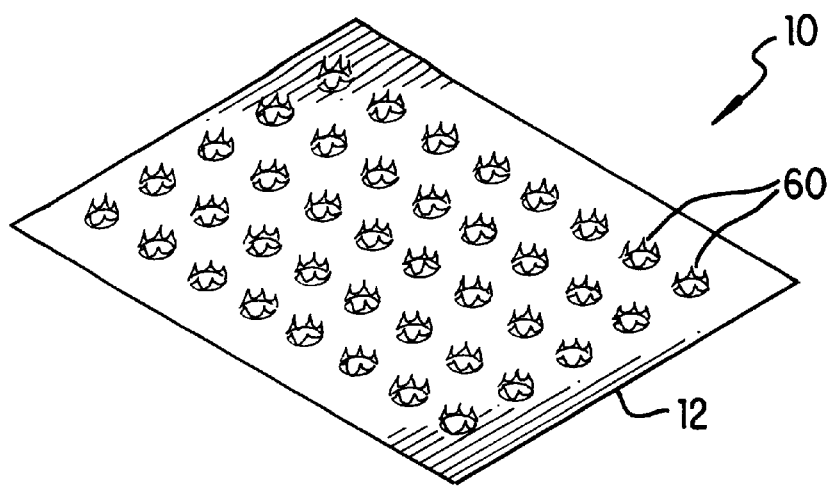
FIG. 1 is a perspective view of a micropenetrator array according to an embodiment of the invention.

Many useful therapeutic agents such as lidocaine, for topical application, and insulin, may be introduced into the body by diffusion into the upper layers of the dermis. The dermis, consisting of live tissue, is highly permeable to fluids, such as the body's own lymphatic fluid. In order, however, to introduce external agents into the dermis from outside the body, it is necessary to traverse the stratus corneum of the epidermis which has extremely low permeability to fluids.

The process whereby therapeutic agents or other substances, liquid or gaseous, are moved into, out of, or through, tissue, whether by suction, diffusion, or by any combination of density or pressure gradients, or otherwise, is referred to as "transport" in this description and in the appended claims. Additionally, as used in this description and in the appended claims, the term "micropenetrator" refers to a sharp protuberance which can be used to puncture the dead skin of the epidermis without penetrating substantially into the sensitive skin of the dermis. By puncturing the epidermis, a micropenetrator may be used effectively to introduce many therapeutic agents into the dermis. The size of the separation in the epidermis required to enable penetration of a particular compound depends upon the specific molecular structure of the compound. In some cases, the size needed to pass a therapeutic agent may be microscopically small, on the order of micrometers. In this description and in the appended claims, the term "microfissure" refers to the separation in the epidermis through which therapeutic agent can be passed into the dermis in accordance with this invention. Microfissures may occur naturally as microscopic cracks in the dermis, or may be induced in the skin, as described, through the puncturing action of micropenetrators.

In order for the therapeutic agent to be passed into the dermis in therapeutically useful quantities, it may be necessary to employ a plurality of microfissures, each conducting a fraction of the fluid agent to the dermis. A method and apparatus employing one or more micropenetrators to introduce fluid through the epidermis into the dermis, and a means of manufacture of an apparatus for the same purpose, will now be described with reference to FIGS. 1–9, in which like reference numerals designate identical or corresponding elements of the invention.

Referring now to FIG. 1, a micropenetrator array is shown in perspective view and designated generally by numeral 10. Micropenetrator array 10 consists of a sheet 12 composed of thin foil. In the preferred embodiment, sheet 12 is a hardened metal such as stainless steel, having a thickness of approximately 0.0005–0.003 inches (0.5–3 mil, or approximately 13–75 microns). Other materials may be employed, as may coatings and treatments of sheet 12, all falling under the present invention as claimed. In this description and in the appended claims, sheet 12 is referred to, also, as a "platen." The areal dimensions of platen 12 are typically on the order of 1 centimeter square, however larger or smaller dimensions are employed depending on the quantity of fluid to be introduced into the body, and the rate at which fluid is advantageously introduced to achieve the requisite diffusion depth, as discussed in greater detail below. Platen 12 is readily manufactured, as discussed below, and readily sterilized to prevent introduction of infectious or toxic materials through the epidermis.

Figure 2:
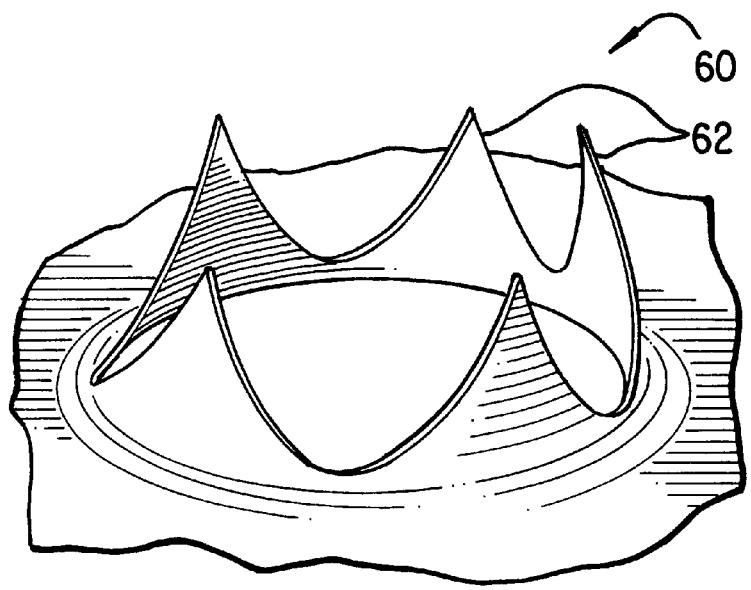
FIG. 2 is a perspective view of a conical micropenetrator according to the embodiment of the invention of FIG. 1.

Micropenetrators are sharp edges produced in platen 12 by disrupting the continuity of platen 12 by an array of cuts, slots 14 (shown in FIG. 7) or protrusions. FIG. 2 shows an embodiment of the present invention in which micropenetrator 60 is created by punching through platen 12 leaving jagged edges 62 through which fluid may be introduced through the stratus corneum. Other shapes of micropenetrator are within the scope of this invention, as discussed further below. The conical or volcano-like shape is shown as an example, though many other shapes of cuts or slots may be employed. In the preferred embodiment, an array of, typically, 10 by 10 micropenetrators, is punched into platen 12. Referring, again, to FIG. 1, the spacing between micropenetrator 60 is on the order of 0.10 inches (~2.5 mm), however the precise absolute and relative dimensions depend on the material and clinical parameters discussed below. In the preferred embodiment, the spacing of the array may be regular, as shown, or random, depending upon the depth diffusion profile required. In the preferred embodiment, the sharp, jagged, and very strong edges 62 of micropenetrators 60, for separating the tissue of the epidermis, are produced by means of the manufacturing process discussed below. When platen 12 is pressed firmly against the skin of the subject, micropenetrators 60 penetrate toward the dermis by approximately the thickness of the typical epidermal layer, or, on the order of 1 mil (~25 microns).

Figure 5:
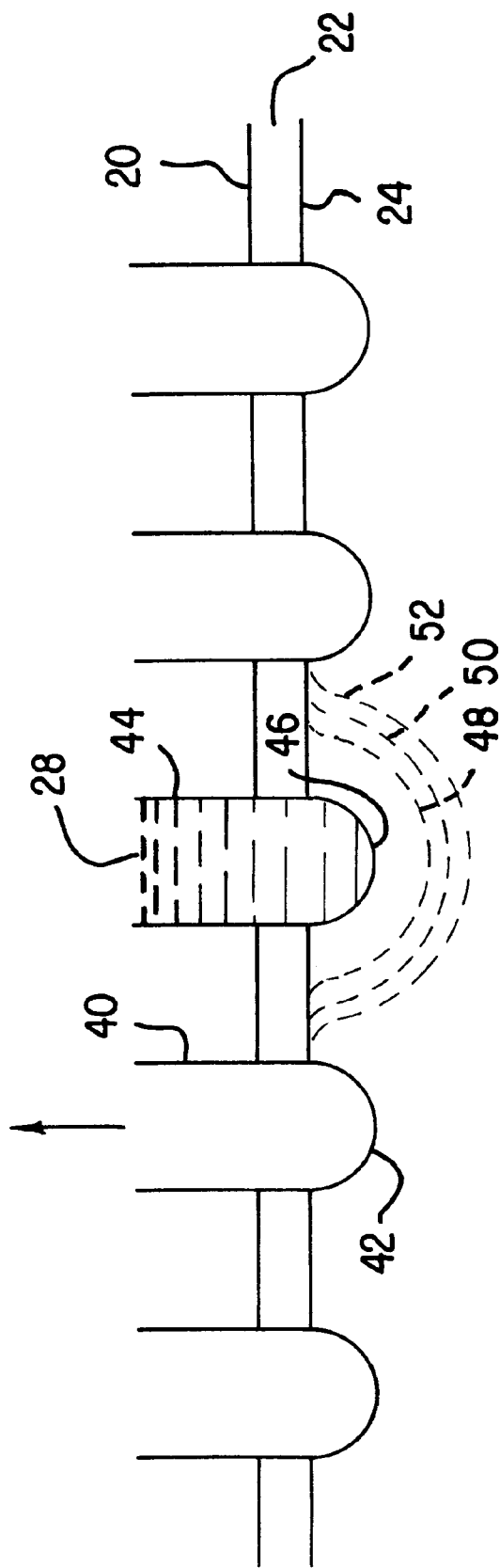
FIG. 5 is a cross-sectional view showing a section of a row of the micropenetrators of FIG. 1 penetrating the skin and further showing contours of equal concentration of agent due jointly to diffusion and suction.

The mechanism for introduction of fluid into the dermis is now described with reference to FIGS. 3–5 where the skin of the subject is shown in cross-section, with skin 20 constituting the interlace between epidermis 22 and the ambient environment. Interface 24 separates epidermis 22 from the dermis. Microfissures 26, as defined above, are separations of the epidermis caused by the cleaving action of micropenetrators. For the introduction of certain fluid agents, it is unnecessary for the micropenetrator to protrude outside the plane of the platen since the epidermis is effectively separated by being drawn by a vacuum around the tight radius of curvature of the slot edges. The precise shape of microfissures 26 may be cylindrical or irregular, and is not critical to this discussion. The micropenetrators may be complete cannulae, however, this is unnecessary in many cases since the surface tension of the fluid and the capillary action at the epidermis provide for the guidance of fluid into microfissures 26.

Whereas a liquid is conventionally injected into the body by imparting to the liquid a pressure higher than the internal pressure within the body, a preferred embodiment of the present invention uses two other principles. One is diffusion—the propensity of a liquid to flow from a place of higher density to a place of lesser density. As is well known in elementary physics, the flow J is proportional to the gradient of the density ρ of liquid, $$J = -a^2 \nabla \rho,$$

where a is the diffusion constant and accounts for the percolation of the fluid through the skin tissue, and, particularly, for the molecular dimensions of the injected agent relative to the porosity of the tissue. The sense of the proportionality reflects the fact that fluid flows away from regions of higher density toward regions of lower density. Since fluid 28 introduced into the system via microfissure 30 is conserved, $$\partial \rho / \partial t = -\nabla \cdot J,$$

which expresses the fact that the flow out of a surface surrounding every infinitesimal volume element equals the decrement in fluid contained within the element. Combination of the last two equations results in a spatial distribution of fluid within the dermal tissue, considering diffusion alone, given by the diffusion equation, $$\partial \rho / \partial t = a^2 \nabla^2 \rho.$$

This behavior reflects the "wicking" action of the skin. Solution of the diffusion equation in three dimensions yields the precise distribution of fluid within the dermal tissue, in particular, the contours of equal concentration of fluid 28 radiate from the bottom surface 32 of the microfissure, with the concentration decreasing nearly exponentially into the dermis. Thus, if contour 34 represents a contour of half-saturation of the tissue, a contour 36 of ¼-saturation is half-again as deep into the dermis as contour 34 is from the bottom surface 32 of the microfissure.

However, for some agents which are beneficially introduced hypodermically, diffusion alone is inadequate to introduce effective quantities of agent into the dermis. The flow, J, of a fluid into a porous medium, such as the dermis, is also governed by pressure gradients, according to $$\partial J / \partial t + RJ = F - \nabla p,$$

where R is an effective resistance (possibly a tensor, taking the structural profile of the skin into account) of the dermis to flow by the particular fluid being introduced; F is the force, if any, applied to inject the fluid into the skin; and p is the field characterizing the pressure within the dermis. A pressure gradient, $\nabla p$, is created in the dermis by application of a vacuum or partial vacuum to a subset of the microfissures 26. Alternatively, the pressure gradient $\nabla p$, may be created by application of a vacuum or partial vacuum external to the epidermis 22, since the epidermis is permeable to the flow of air from the dermis outward. The effect of applying a vacuum or partial vacuum at a microfissure 40 is shown in FIG. 4. The bottom surface 42 is at the pressure $p_2$ of the partial vacuum applied, while isobaric contours 44, 46, and 48 show successively increasing pressures, tending to the internal pressure $p_0$ of the dermis, which, due to the permeability of the epidermis, is substantially in equilibrium with the ambient pressure at the outside surface of the epidermis, that is, typically, at the ambient atmospheric pressure. Isobaric contours 43, 45 and 47 denote zones of the porous medium between any two of which a pressure gradient is said to exist.

To derive the distribution of liquid in the dermis as a function of time, when vacuum is applied to some portions of the region of skin to which micropenetrators have been applied and liquid is applied to the dermis through microfissures, the diffusion equation is solved subject to the pressure constraints. The effect of applying a vacuum or partial vacuum is shown in FIG. 5. A vacuum is applied at microfissure 40, or, alternatively, through the epidermis, creating a surface of low pressure at the bottom surface 42 of microfissure 40. The neighboring microfissure 44 allows liquid 28 to pass through epidermis 22. By virtue of the pressure gradient created within the dermis, contours of equal concentration 48, 50, and 52 show more uniform penetration of the liquid into the dermis than in the absence of an applied vacuum, as well as a deeper penetration. The path of transport of liquid 28 into the porous medium is described by path 54 which is orthogonal to contours 48, 50, and 52 and is directed from microfissure 44 into which liquid 28 is introduced and toward microfissure 40 to which a partial vacuum is applied. The scenario of path 54 traversing contours 48, 50 and 52 from zones of higher pressure toward zones of lower pressure may be repeated many times, with paths emanating from each microfissure 44 of higher pressure and directed toward each microfissure 40 of lower pressure.

The diffusion constant defines a scale which is a volume per depth-time product, in terms of which the size and spacing of the microholes and the differential pressure applied between the liquid and the vacuum plena are optimized to provide penetration of the requisite depth for a therapeutic agent of given molecular structure.

In order to provide a given area of interface between the liquid and the dermis, the ratio of microfissure diameter to center-spacing must be traded off against total number of microfissures. This requires solution of the above equations for the material parameters of the system which include the diffusion constant, a, of the particular agent in tissue, and the effective resistance R.

Figure 6:
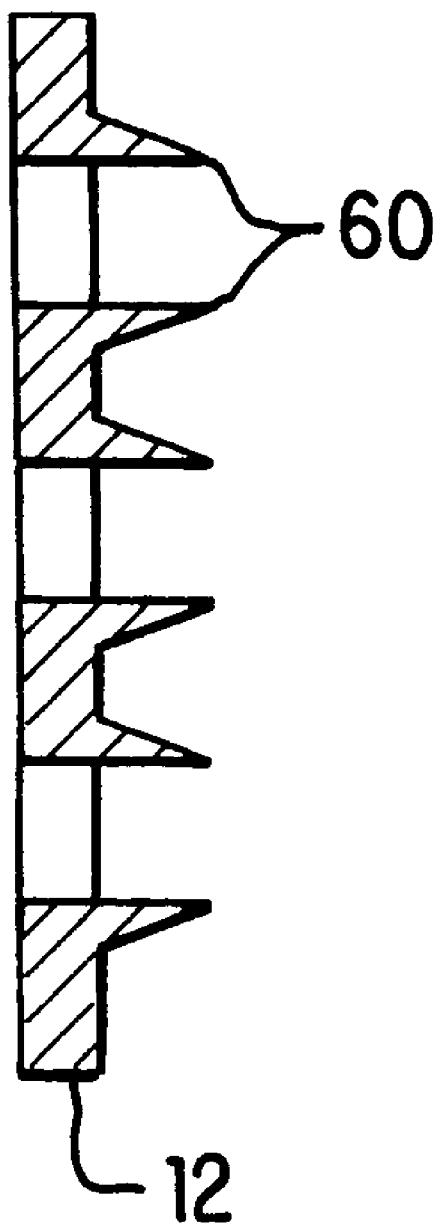
FIG. 6 is a cross-sectional view of a row of the micropenetrators of FIGS. 1 and 2 according to an embodiment of the invention.
Figure 7:
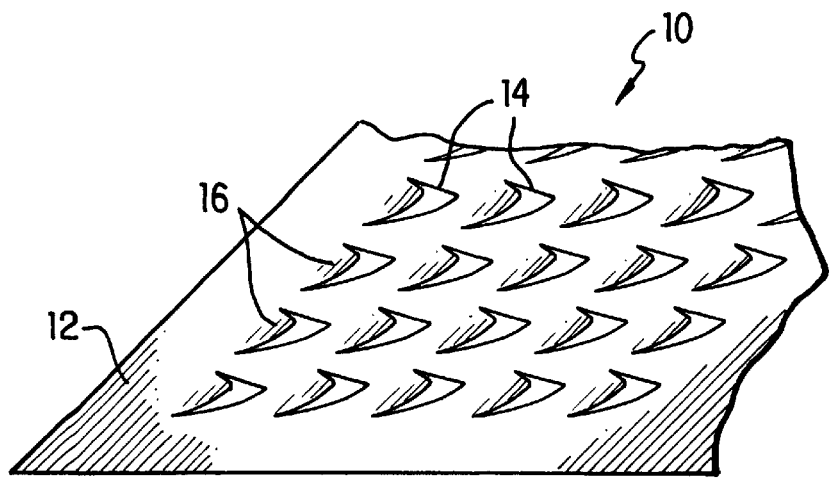
FIG. 7 is a perspective view of a micropenetrator array according to an alternate embodiment of the invention.
Figure 8:
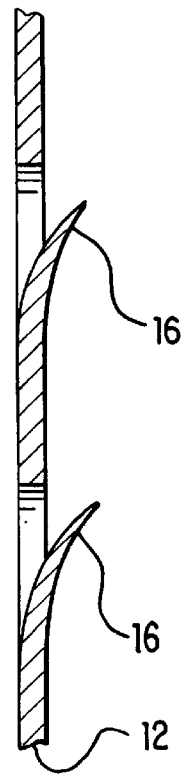
FIG. 8 is a cross-sectional view of a row of the micropenetrators of FIG. 7 according to an alternate embodiment of the invention.

FIG. 6 shows the micropenetrator shape of FIGS. 1 and 2 in silhouette. An alternate shape of micropenetrator may now be appreciated with reference to FIG. 7. In this alternate embodiment of the invention, micropenetrators are sharp edges produced in platen 12 by disrupting the continuity of platen 12 by an array of cuts or slots 14. The chevron or half-moon shape is shown as an example, though many other shapes of cuts or slots may be employed. The slots, in this embodiment, are on the order of 0.050 inches (~1.3 mm) in linear dimension. The micropenetrators, in this embodiment, for separating the tissue of the epidermis, are produced by bending tongues 16 slightly out of the plane of platen 12 so that, when platen 12 is pressed firmly against the skin of the subject, the micropenetrators penetrate toward the dermis by approximately the thickness of the typical epidermal layer, or, on the order of 1 mil (~25 microns). In FIG. 8, tongues 16 of FIG. 7 are shown, in cross-section, as depressed out of the plane of platen 12.

Figure 9:
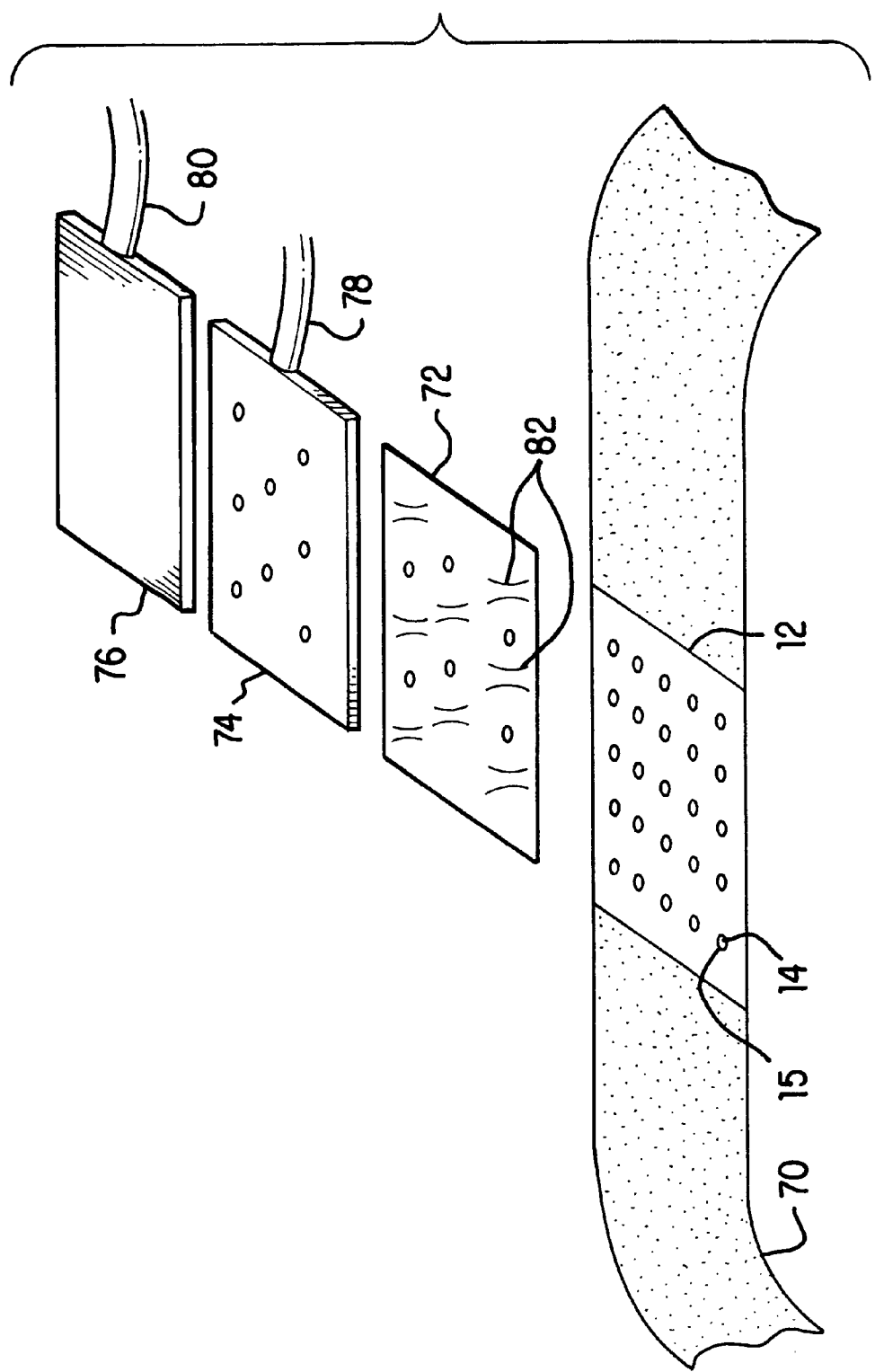
FIG. 9 is an exploded view of an embodiment of the invention showing dual plena for the joint application of suction and liquid agent.

In order to create the configuration of alternating subregions of low pressure and injected fluid, various embodiments may be employed. Referring now to FIG. 9, in the preferred embodiment, platen 12 is secured to a region of the skin of the subject by means of an adhesive material 70. Dual manifold 72 provides coupling between a subset of slots 14 and plenum 74, and through-passages 82 to allow air to be drawn between plenum 76 and a complementary subset of slots 14 without communication with plenum 74. A vacuum is drawn through hose 80 on plenum 76, and, thereby, via the interconnected slots 14, on the skin of the subject. Means, such as mechanical pumps or chemical reactions, are well known in the art for production of a vacuum or partial vacuum. While a vacuum is being drawn via plenum 76, fluid may be introduced into the dermis through hose 78, or, more generally, from any kind of reservoir, through plenum 74, and interconnected slots 14. The fluid is ordinarily at ambient pressure, however, in cases where more rapid infusion into the skin is indicated, additional pressure may be applied to the fluid via hose 78 and plenum 74. The amount and rate of transport may additionally be monitored by sensors of volume or concentration of fluid within the skin, or, alternatively by sensors of flow rate or volume of fluid within the delivery device, or, in a further alternate embodiment, by means of monitoring some biological response such as blood glucose level, for example. In applications where this is desirable, the rate of introduction of the fluid into the dermis may be regulated by a controller, in a closed loop, in response to quantities measured by any of the aforementioned sensors.

In yet another alternate embodiment, a single plenum 76 is employed, sealing platen 12 to all passage of air other than through slots 14. In this embodiment, platen 12 is positioned adjacent to a region of the skin of a subject and secured by an adhesive material 70, by vacuum suction, or by directly applied force. A vacuum is drawn through slots 14 of platen 12 by withdrawing air through vacuum hose 80, using conventional pumping means. Not only is the skin surface drawn up against platen 12 by the vacuum, but, additionally, a pressure gradient is created within the dermis of the subject since air is also drawn through the epidermis due to its finite permeability to air. Additionally, micropenetrators, which are edges 15 of slots 14, are introduced into the epidermis by virtue of the skin having been drawn against platen 12. By operation of an external valve (not shown), fluid is introduced into hose 80, backfilling plenum 76, and is drawn through slots 14 and micropenetrators 16 into the dermis.

The methods described herein may be applied in other applications besides the clinical applications in terms of which the invention has been described. Generally, the invention may be applied to achieve a particular distribution of a liquid within a porous medium, where the medium is accessible from only one side. The described embodiments of the invention are intended to be merely exemplary and numerous variations and modifications will be apparent to those skilled in the art. All such variations and modifications are intended to be within the scope of the present invention as defined in the appended claims.

I claim:

1. A method for transporting a substance across an outer boundary of a permeable medium having at least one microfissure, the method comprising:

a. creating a pressure gradient along at least one path, each path running parallel to the outer boundary of the permeable medium from a first zone of the permeable medium to a second zone of the permeable medium proximate to the first zone, the first and second zones each being proximate to the outer boundary of the permeable medium; and b. causing transport of the substance across the outer boundary of the permeable medium through at least one microfissure.

2. A method according to claim 1, wherein the substance is drawn into permeable medium.

3. A method according to claim 1, wherein the substance is drawn out of the permeable medium.

4. A method according to claim 1, wherein the substance is a liquid.

5. A method according to claim 1, wherein the substance is a therapeutic agent.

6. A method according to claim 1, wherein the permeable medium is body tissue.

7. A method according to claim 1, wherein the step of creating a pressure gradient along at least one path running between zones of the permeable medium includes puncturing at least one microfissure in the outer boundary of the permeable medium with at least one micropenetrator.

8. A method according to claim 1, wherein the step of creating a pressure gradient along at least one path running between zones of the permeable medium includes applying suction to a portion of the outer boundary of the permeable medium.

9. A method according to claim 1, wherein the step of creating a pressure gradient between zones of the permeable medium includes puncturing a plurality of microfissures in the permeable medium with a plurality of micropenetrators and applying suction to a subset of the micropenetrators.

10. A method according to claim 1, wherein the step of creating a pressure gradient between zones of the permeable medium includes puncturing a plurality of microfissures in the permeable medium with a plurality of micropenetrators and applying suction to a subset of the microfissures.

11. A method according to claim 1, wherein the step of puncturing at least one microfissure into the outer surface of the permeable medium with at least one micropenetrator includes applying suction to a portion of the outer boundary of the permeable medium substantially surrounding the contact between at least one micropenetrator and the outer boundary of the permeable medium.

12. An apparatus for causing the transport of a substance across an outer boundary of a permeable medium, the apparatus comprising:

a. a micropenetrator for penetrating the outer surface of a first zone of the permeable medium to a depth no greater than 1000 micrometers, thereby creating a microfissure;

b. a vacuum arrangement that applies a partial vacuum to a second zone of the permeable medium, the second zone proximate to the first zone, thereby creating a pressure gradient along a path running from the microfissure to the second zone of the permeable medium, so that the pressure at the second zone is below ambient pressure external to the outer boundary of the permeable medium; and c. a reservoir for supplying a substance to the micropenetrator so as to cause transport of the substance into the permeable medium.

13. An apparatus according to claim 12, further comprising:

a. at least one sensor having an output for monitoring the quantity of the substance transported across the outer boundary of the permeable medium; and b. a controller for regulating the rate of supply of the substance by the reservoir based on the output of each sensor.

14. An apparatus according to claim 12, further comprising:

a. at least one sensor having an output for monitoring a biological response to transport of the substance across the outer boundary of the permeable medium; and b. a controller for regulating the rate of supply of the substance supplied by the reservoir based on the output of each sensor.

15. An apparatus according to claim 1 further comprising a partial vacuum for drawing the outer surface of the permeable medium against at least one micropenetrator.

16. An apparatus for transporting a substance across the outer boundary of a permeable medium, the apparatus comprising:

a. a platen having a first and a second orifice, the first orifice characterized by a first pressure and the second orifice characterized by a second pressure, the difference between the first pressure and the second pressure causing a pressure gradient parallel to the outer boundary of the permeable medium;

b. at least one micropenetrator coupled to the platen for cleaving at least one microfissure in the outer boundary of the permeable medium; and c. an arrangement for guiding a substance into the permeable medium via the at least one microfissure based at least in part on the pressure gradient.

17. A method of manufacture for producing an apparatus for transporting a substance across the outer boundary of a permeable medium, the method comprising:

a. punching an array of protrusions having central orifices in the surface of a thin planar platen;

b. coupling a plenum to a first subset of the orifices in the platen; and c. applying suction to a second subset of the orifices in the platen.

18. A method of manufacture according to claim 17, wherein the step of punching an array of protrusions includes punching conical protrusions.

19. A method of manufacture for producing an apparatus for transporting a substance across the outer boundary of a permeable medium, the method comprising:

a. punching an array of peninsular tongues in the surface of a thin planar platen;

b. depressing the peninsular tongues below the surface of the platen such as to create orifices in the platen;

c. coupling a first plenum to a first subset of the orifices in the platen;

d. coupling a second plenum to a second set of the orifices in the platen.

20. A method according to claim 1, wherein the pressure at the second zone is below ambient pressure exterior to the outer boundary of the porous medium.

21. A method for transporting a substance across the outer boundary of a permeable medium, the method comprising:

a. providing at least one micropenetrator for cleaving at least one microfissure in the outer boundary of the permeable medium;

b. creating a pressure gradient parallel to the outer boundary of the permeable medium; and c. guiding a substance into the permeable medium via the at least one microfissure on the basis at least of the pressure gradient.

22. A method of manufacture for producing an apparatus for transporting a substance across the outer boundary of a porous medium, the method comprising:

a. punching an array of protrusions having central orifices in the surface of a thin planar platen;

b. coupling a first plenum to a first subset of the orifices in the platen;

c. coupling a second plenum to a second set of the orifices in the platen.

\* \* \* \* \*

UNITED STATES PATENT AND TRADEMARK OFFICE
CERTIFICATE OF CORRECTION

PATENT NO. : 5,983,136
DATED       : November 9, 1999
INVENTOR(S) : Kamen

It is certified that error appears in the above-identified patent and that said Letters Patent is hereby corrected as shown below:

Col. 8, Line 19 change "into permeable" to --into the permeable--

Signed and Sealed this

Twenty-third Day of May, 2000

Attest:

Q. TODD DICKINSON

*Attesting Officer*                    *Director of Patents and Trademarks*